US010113543B2

United States Patent
Rotem et al.

(10) Patent No.: US 10,113,543 B2
(45) Date of Patent: Oct. 30, 2018

(54) FINGER TYPE PERISTALTIC PUMP COMPRISING A RIBBED ANVIL

(71) Applicant: Q-CORE MEDICAL LTD., Petach Tikva (IL)

(72) Inventors: Shachar Rotem, M.P. Hefer (IL); Ori Goldor, Amikam (IL)

(73) Assignee: Q-CORE MEDICAL LTD., Petach Tikva (IL)

( * ) Notice: Subject to any disclaimer, the term of this patent is extended or adjusted under 35 U.S.C. 154(b) by 108 days.

(21) Appl. No.: 13/681,440

(22) Filed: Nov. 20, 2012

(65) Prior Publication Data

US 2013/0142670 A1   Jun. 6, 2013

Related U.S. Application Data

(63) Continuation of application No. 12/514,310, filed as application No. PCT/IL2007/001398 on Nov. 13, 2007, now Pat. No. 8,337,168.

(30) Foreign Application Priority Data

Nov. 13, 2006 (IL) .......................... 179231

(51) Int. Cl.
  *F04B 43/12*  (2006.01)
  *F04B 43/08*  (2006.01)
  *A61M 5/142*  (2006.01)

(52) U.S. Cl.
  CPC ............ *F04B 43/12* (2013.01); *F04B 43/082* (2013.01); *A61M 5/14228* (2013.01)

(58) Field of Classification Search
  CPC .... F04B 43/12; F04B 43/082; A61M 5/14228
  (Continued)

(56) References Cited

U.S. PATENT DOCUMENTS 2,056,322 A   10/1936 Hoppe
2,393,838 A   1/1946 Tarbox
(Continued)

FOREIGN PATENT DOCUMENTS

DE   10118086 A1   7/2002
EP   0215249 A1   3/1987
(Continued)

OTHER PUBLICATIONS

Honeywell Sensing and Control, "FSSI500NSB force sensor", Golden Valley, Minnesota, USA, 1998-2004 http://sccatalog.honeywell.com/imc/printfriendly.asp?FAM-force&PN~FSSI500NSB (5 pages).
(Continued)

*Primary Examiner* — Peter J Bertheaud
*Assistant Examiner* — Dnyanesh Kasture
(74) *Attorney, Agent, or Firm* — The Roy Gross Law Firm, LLC; Roy Gross

(57) ABSTRACT

The present invention includes a finger-type peristaltic pump with a ribbed anvil. According to some embodiments, a finger type peristaltic pump may comprise a plurality of pressing fingers, an infusion tube and a passive interfacing mechanism. The passive interfacing mechanism may comprise a channel, groove or other suitable mount for placing and mounting an infusion tube such that the pressing fingers are positioned on one side of the tube and the ribbed anvil on the opposite side. The pressing fingers may be positioned to apply an approximately perpendicular force on the tube, pressing it against the ribbed anvil, thus causing a pumping action.

15 Claims, 3 Drawing Sheets

(58) Field of Classification Search
USPC .............................. 417/474–477.14; 604/153
See application file for complete search history.

(56) References Cited

U.S. PATENT DOCUMENTS

| | | | |
|---|---|---|---|
| 2,743,898 A | 5/1956 | King | |
| 2,981,115 A | 4/1961 | Beguin | |
| 3,443,585 A | 5/1969 | Reinicke | |
| 3,511,583 A | 5/1970 | Brown | |
| 3,677,667 A | 7/1972 | Morrison | |
| 3,778,195 A * | 12/1973 | Bamberg | 417/474 |
| 3,982,722 A | 9/1976 | Bernard | |
| 3,982,725 A | 9/1976 | Clark | |
| 4,014,318 A | 3/1977 | Dockum et al. | |
| 4,039,269 A | 8/1977 | Pickering | |
| 4,155,362 A | 5/1979 | Jess | |
| 4,178,138 A * | 12/1979 | Iles | 417/360 |
| 4,236,880 A | 12/1980 | Archibald | |
| 4,270,532 A | 6/1981 | Franetzki et al. | |
| 4,273,121 A * | 6/1981 | Jassawalla | A61M 5/14224 |
| | | | 128/DIG. 12 |
| 4,290,346 A * | 9/1981 | Bujan | 92/96 |
| 4,320,781 A | 3/1982 | Bouvet et al. | |
| 4,373,525 A | 2/1983 | Kobayashi | |
| 4,450,375 A | 5/1984 | Siegal | |
| 4,479,797 A * | 10/1984 | Kobayashi et al. | 604/153 |
| 4,489,863 A | 12/1984 | Horchos et al. | |
| 4,493,706 A | 1/1985 | Borsanyi et al. | |
| 4,650,469 A * | 3/1987 | Berg et al. | 604/131 |
| 4,671,792 A | 6/1987 | Borsanyi | |
| 4,682,135 A | 7/1987 | Yamakawa | |
| 4,690,673 A | 9/1987 | Bloomquist | |
| 4,725,205 A | 2/1988 | Cannon et al. | |
| 4,728,265 A | 3/1988 | Cannon | |
| 4,741,736 A | 5/1988 | Brown | |
| 4,748,003 A | 5/1988 | Riley | |
| 4,755,168 A | 7/1988 | Romanelli et al. | |
| 4,836,752 A | 6/1989 | Burkett | |
| 4,867,744 A | 9/1989 | Borsanyi | |
| 4,893,991 A * | 1/1990 | Heminway | F04B 43/082 |
| | | | 417/474 |
| 4,927,411 A | 5/1990 | Pastrone et al. | |
| 4,954,046 A | 9/1990 | Irvin et al. | |
| 4,954,256 A | 9/1990 | Degen et al. | |
| 4,978,335 A | 12/1990 | Arthur, III | |
| 5,074,756 A | 12/1991 | Davis | |
| 5,078,683 A | 1/1992 | Sancoff et al. | |
| 5,088,904 A | 2/1992 | Okada | |
| 5,096,385 A | 3/1992 | Georgi et al. | |
| 5,103,211 A | 4/1992 | Daoud et al. | |
| 5,151,019 A | 9/1992 | Danby et al. | |
| 5,152,680 A | 10/1992 | Okada | |
| 5,165,874 A | 11/1992 | Sancoff et al. | |
| 5,213,483 A | 5/1993 | Flaherty et al. | |
| 5,219,327 A | 6/1993 | Okada | |
| 5,222,946 A | 6/1993 | Kamen | |
| 5,246,347 A | 9/1993 | Davis | |
| 5,257,978 A | 11/1993 | Haber et al. | |
| 5,286,176 A | 2/1994 | Bonin | |
| 5,290,158 A | 3/1994 | Okada | |
| 5,308,333 A | 5/1994 | Skakoon | |
| 5,322,422 A * | 6/1994 | Natwick | A61M 5/14228 |
| | | | 417/474 |
| 5,338,157 A | 8/1994 | Blomquist | |
| 5,395,320 A | 3/1995 | Padda et al. | |
| 5,429,485 A | 7/1995 | Dodge | |
| 5,485,408 A | 1/1996 | Blomquist | |
| 5,499,969 A | 3/1996 | Beuchat et al. | |
| 5,509,439 A | 4/1996 | Tantardini | |
| 5,527,295 A | 6/1996 | Wing | |
| 5,542,826 A | 8/1996 | Warner | |
| 5,569,188 A | 10/1996 | Mackool | |
| 5,575,309 A | 11/1996 | Connell | |
| 5,575,631 A | 11/1996 | Jester | |
| 5,577,891 A | 11/1996 | Loughnane et al. | |
| 5,584,667 A | 12/1996 | Davis | |
| 5,593,134 A | 1/1997 | Steber et al. | |
| 5,601,420 A * | 2/1997 | Warner et al. | 417/474 |
| 5,628,619 A | 5/1997 | Wilson | |
| 5,658,250 A | 8/1997 | Blomquist et al. | |
| 5,658,252 A | 8/1997 | Johnson | |
| 5,660,529 A | 8/1997 | Hill | |
| 5,669,877 A | 9/1997 | Blomquist | |
| 5,683,233 A | 11/1997 | Moubayed et al. | |
| 5,695,473 A | 12/1997 | Olsen | |
| 5,704,584 A | 1/1998 | Winterer et al. | |
| 5,742,519 A | 4/1998 | McClendon et al. | |
| 5,782,805 A | 7/1998 | Meinzer et al. | |
| 5,788,669 A | 8/1998 | Peterson | |
| 5,791,880 A | 8/1998 | Wilson | |
| 5,791,881 A | 8/1998 | Moubayed et al. | |
| 5,803,712 A | 9/1998 | Davis et al. | |
| 5,807,322 A | 9/1998 | Lindsey et al. | |
| 5,810,323 A | 9/1998 | Winterer et al. | |
| 5,853,386 A | 12/1998 | Davis et al. | |
| 5,876,370 A | 3/1999 | Blomquist | |
| 5,888,052 A | 3/1999 | Hill | |
| 5,896,076 A | 4/1999 | Van Namen | |
| 5,909,724 A | 6/1999 | Nishimura et al. | |
| 5,924,852 A | 7/1999 | Moubayed et al. | |
| 5,935,099 A | 8/1999 | Peterson et al. | |
| 5,935,106 A | 8/1999 | Olsen | |
| 5,943,633 A | 8/1999 | Wilson et al. | |
| 5,954,485 A | 9/1999 | Johnson et al. | |
| 5,980,490 A | 11/1999 | Tsoukalis | |
| 5,996,964 A | 12/1999 | Ben-Shalom | |
| 6,024,539 A | 2/2000 | Blomquist | |
| 6,095,189 A | 8/2000 | Ben-Shalom | |
| 6,110,153 A | 8/2000 | Davis et al. | |
| 6,146,109 A | 11/2000 | Davis et al. | |
| 6,164,921 A | 12/2000 | Moubayed et al. | |
| 6,165,874 A | 12/2000 | Powell et al. | |
| RE37,074 E | 2/2001 | Danby et al. | |
| 6,203,296 B1 | 3/2001 | Ray et al. | |
| 6,213,723 B1 | 4/2001 | Danby et al. | |
| 6,213,739 B1 * | 4/2001 | Phallen et al. | 417/478 |
| 6,234,773 B1 * | 5/2001 | Hill et al. | 417/474 |
| 6,241,704 B1 | 6/2001 | Peterson et al. | |
| 6,261,262 B1 | 7/2001 | Briggs et al. | |
| 6,280,408 B1 | 8/2001 | Sipin | |
| 6,312,227 B1 | 11/2001 | Davis | |
| 6,339,410 B1 | 1/2002 | Milner et al. | |
| 6,347,553 B1 | 2/2002 | Morris et al. | |
| 6,371,732 B1 | 4/2002 | Moubayed et al. | |
| 6,422,057 B1 | 7/2002 | Anderson | |
| 6,450,773 B1 | 9/2002 | Upton | |
| 6,475,180 B2 | 11/2002 | Peterson et al. | |
| 6,519,569 B1 | 2/2003 | White et al. | |
| 6,537,244 B2 | 3/2003 | Paukovits et al. | |
| 6,544,171 B2 | 4/2003 | Beetz et al. | |
| 6,558,347 B1 | 5/2003 | Jhuboo et al. | |
| 6,572,604 B1 | 6/2003 | Platt et al. | |
| 6,622,542 B2 | 9/2003 | Derek et al. | |
| 6,648,861 B2 | 11/2003 | Platt et al. | |
| 6,692,241 B2 | 2/2004 | Watanabe et al. | |
| 6,733,476 B2 | 5/2004 | Christenson et al. | |
| 6,742,992 B2 | 6/2004 | Davis | |
| 6,749,587 B2 | 6/2004 | Flaherty | |
| 6,768,425 B2 | 7/2004 | Flaherty et al. | |
| 6,788,199 B2 | 9/2004 | Crabtree et al. | |
| 6,790,198 B1 | 9/2004 | White et al. | |
| 6,902,549 B2 | 6/2005 | Marmaropoulos et al. | |
| 6,942,473 B2 | 9/2005 | Abrahamson et al. | |
| 7,018,361 B2 | 3/2006 | Gillespie, Jr. et al. | |
| 7,022,075 B2 | 4/2006 | Grunwald et al. | |
| 7,048,720 B1 | 5/2006 | Thorne, Jr. et al. | |
| 7,059,840 B2 | 6/2006 | Corwin et al. | |
| 7,122,026 B2 | 10/2006 | Rogers et al. | |
| 7,131,966 B1 | 11/2006 | Tamari | |
| 7,163,385 B2 | 1/2007 | Gharib et al. | |
| 7,347,836 B2 | 3/2008 | Peterson et al. | |
| 7,525,432 B2 | 4/2009 | Jackson | |
| 7,556,481 B2 | 7/2009 | Moubayed | |
| 7,645,258 B2 | 1/2010 | White et al. | |

(56) References Cited

U.S. PATENT DOCUMENTS

| | | |
|---|---|---|
| 7,654,976 B2 | 2/2010 | Peterson et al. |
| 7,695,255 B2 | 4/2010 | Ben-Shalom et al. |
| 7,698,156 B2 | 4/2010 | Martucci et al. |
| 7,704,227 B2 | 4/2010 | Moberg et al. |
| 7,762,795 B2 | 7/2010 | Moubayed |
| 7,840,260 B2 | 11/2010 | Epley |
| 7,892,332 B2 | 2/2011 | Prisco et al. |
| 7,896,834 B2 | 3/2011 | Smisson, III et al. |
| 7,935,102 B2 | 5/2011 | Breznock et al. |
| 7,938,796 B2 | 5/2011 | Moubayed et al. |
| 7,963,946 B2 | 6/2011 | Moubayed et al. |
| 7,998,121 B2 | 8/2011 | Stringham |
| 8,025,634 B1 | 9/2011 | Moubayed et al. |
| 8,029,253 B2 | 10/2011 | Rotem et al. |
| 8,142,400 B2 | 3/2012 | Rotem et al. |
| 8,182,445 B2 | 5/2012 | Moubayed et al. |
| 8,197,235 B2 | 6/2012 | Davis |
| 8,214,231 B2 | 7/2012 | Martucci et al. |
| 8,234,128 B2 | 7/2012 | Martucci et al. |
| 8,241,018 B2 | 8/2012 | Harr |
| 8,257,654 B2 | 9/2012 | Maus et al. |
| 8,308,457 B2 | 11/2012 | Rotem et al. |
| 8,334,768 B2 | 12/2012 | Eaton et al. |
| 8,337,168 B2 | 12/2012 | Rotem et al. |
| 8,343,111 B2 | 1/2013 | Beck et al. |
| 8,352,290 B2 | 1/2013 | Bartz et al. |
| 8,363,583 B2 | 1/2013 | Jia et al. |
| 8,371,832 B2 | 2/2013 | Rotem et al. |
| 8,444,587 B2 | 5/2013 | Kelly et al. |
| 8,489,427 B2 | 7/2013 | Simpson et al. |
| 8,535,025 B2 | 9/2013 | Rotem et al. |
| 8,579,816 B2 | 11/2013 | Kamath et al. |
| 8,666,367 B2 | 3/2014 | Sharp et al. |
| 8,672,875 B2 | 3/2014 | Vanderveen et al. |
| 8,678,793 B2 | 3/2014 | Goldor et al. |
| 8,920,144 B2 | 12/2014 | Rotem et al. |
| 9,056,160 B2 | 6/2015 | Rotem et al. |
| 2001/0029321 A1 | 10/2001 | Beetz et al. |
| 2002/0056675 A1 | 5/2002 | Hegde |
| 2002/0094287 A1 | 7/2002 | Davis |
| 2002/0156402 A1 | 10/2002 | Woog et al. |
| 2002/0165503 A1 | 11/2002 | Morris et al. |
| 2003/0034887 A1 | 2/2003 | Crabtree et al. |
| 2003/0040700 A1 | 2/2003 | Hickle et al. |
| 2003/0065536 A1 | 4/2003 | Hansen et al. |
| 2003/0109988 A1 | 6/2003 | Geissler et al. |
| 2003/0140928 A1 | 7/2003 | Bui et al. |
| 2003/0141981 A1 | 7/2003 | Bui et al. |
| 2003/0182586 A1 | 9/2003 | Numano |
| 2004/0167804 A1 | 8/2004 | Simpson et al. |
| 2004/0172222 A1 | 9/2004 | Simpson et al. |
| 2004/0181314 A1 | 9/2004 | Zaleski |
| 2004/0191112 A1 | 9/2004 | Hill et al. |
| 2004/0204673 A1 | 10/2004 | Flaherty |
| 2004/0204685 A1 | 10/2004 | Wright et al. |
| 2004/0235446 A1 | 11/2004 | Flaherty et al. |
| 2005/0001369 A1 | 1/2005 | Cross |
| 2005/0022274 A1 | 1/2005 | Campbell et al. |
| 2005/0055242 A1 | 3/2005 | Bello et al. |
| 2005/0088409 A1 | 4/2005 | Van Berkel |
| 2005/0112001 A1 | 5/2005 | Bahnen et al. |
| 2005/0171501 A1 | 8/2005 | Kelly |
| 2005/0191196 A1 | 9/2005 | Tanner et al. |
| 2005/0214146 A1 | 9/2005 | Corwin et al. |
| 2006/0051218 A1 | 3/2006 | Harttig |
| 2006/0083644 A1 | 4/2006 | Zumbrum et al. |
| 2006/0173419 A1 | 8/2006 | Malcolm |
| 2006/0213249 A1 | 9/2006 | Uram et al. |
| 2007/0032098 A1 | 2/2007 | Bowles et al. |
| 2007/0048161 A1 | 3/2007 | Moubayed |
| 2007/0060872 A1 | 3/2007 | Hall et al. |
| 2007/0118405 A1 | 5/2007 | Campbell et al. |
| 2007/0135866 A1 | 6/2007 | Baker et al. |
| 2007/0154336 A1 | 7/2007 | Miyazaki et al. |
| 2007/0217931 A1 | 9/2007 | Estes et al. |
| 2007/0269324 A1 | 11/2007 | Goldor et al. |
| 2008/0015506 A1 | 1/2008 | Davis |
| 2008/0065007 A1 | 3/2008 | Peterson et al. |
| 2008/0065016 A1 | 3/2008 | Peterson et al. |
| 2008/0067462 A1 | 3/2008 | Miller et al. |
| 2008/0071251 A1 | 3/2008 | Moubayed et al. |
| 2008/0095649 A1 | 4/2008 | Ben-Shalom et al. |
| 2008/0144560 A1 | 6/2008 | Jia et al. |
| 2008/0145249 A1 | 6/2008 | Smisson et al. |
| 2008/0146995 A1 | 6/2008 | Smisson et al. |
| 2008/0275307 A1 | 11/2008 | Poschmann |
| 2009/0088675 A1 | 4/2009 | Kelly et al. |
| 2009/0163864 A1 | 6/2009 | Breznock et al. |
| 2009/0203329 A1 | 8/2009 | White et al. |
| 2009/0221964 A1 | 9/2009 | Rotem et al. |
| 2009/0240201 A1 | 9/2009 | Rotem et al. |
| 2009/0270810 A1 | 10/2009 | DeBelser et al. |
| 2009/0300507 A1 | 12/2009 | Raghavan et al. |
| 2009/0317268 A1 | 12/2009 | Rotem et al. |
| 2010/0016781 A1 | 1/2010 | Nakayama et al. |
| 2010/0036322 A1 | 2/2010 | Rotem |
| 2010/0082001 A1 | 4/2010 | Beck et al. |
| 2010/0168545 A1 | 7/2010 | Kamath et al. |
| 2010/0211002 A1 | 8/2010 | Davis |
| 2010/0228223 A1 | 9/2010 | Williams et al. |
| 2010/0234708 A1 | 9/2010 | Buck et al. |
| 2010/0279652 A1 | 11/2010 | Sharp et al. |
| 2011/0148624 A1 | 6/2011 | Eaton et al. |
| 2011/0152772 A1 | 6/2011 | Rotem et al. |
| 2011/0152831 A1 | 6/2011 | Rotem et al. |
| 2011/0167133 A1 | 7/2011 | Jain |
| 2011/0251856 A1 | 10/2011 | Maus et al. |
| 2011/0264043 A1 | 10/2011 | Kotnik et al. |
| 2011/0276000 A1 | 11/2011 | Stringham |
| 2011/0282291 A1 | 11/2011 | Ciccone |
| 2011/0318208 A1 | 12/2011 | Goldor et al. |
| 2012/0059389 A1 | 3/2012 | Larson et al. |
| 2012/0062387 A1 | 3/2012 | Vik et al. |
| 2012/0136305 A1 | 5/2012 | Gagliardoni et al. |
| 2012/0241525 A1 | 9/2012 | Borges et al. |
| 2013/0006666 A1 | 1/2013 | Schneider et al. |
| 2013/0046508 A1 | 2/2013 | Sur et al. |
| 2013/0116620 A1 | 5/2013 | Rotem et al. |
| 2013/0116623 A1 | 5/2013 | Rotem et al. |
| 2013/0142670 A1 | 6/2013 | Rotem et al. |
| 2013/0209275 A1 | 8/2013 | Rotem et al. |
| 2013/0279370 A1 | 10/2013 | Eitan et al. |
| 2013/0345623 A1 | 12/2013 | Kopperschmidt et al. |
| 2014/0005631 A1 | 1/2014 | Rotem et al. |
| 2014/0119954 A1 | 5/2014 | Schweitzer et al. |
| 2014/0197824 A1 | 7/2014 | Gillespie et al. |
| 2014/0222377 A1 | 8/2014 | Bitan et al. |
| 2014/0276564 A1 | 9/2014 | Schneider |
| 2014/0369872 A1 | 12/2014 | Goldor et al. |
| 2014/0378901 A1 | 12/2014 | Rotem et al. |
| 2015/0038187 A1 | 2/2015 | Ho et al. |
| 2015/0073338 A1 | 3/2015 | Waldhoff et al. |
| 2015/0105726 A1 | 4/2015 | Qi et al. |
| 2015/0137988 A1 | 5/2015 | Gravenstein et al. |
| 2015/0141955 A1 | 5/2015 | Ruchti et al. |
| 2015/0172921 A1 | 6/2015 | Wang et al. |
| 2015/0182694 A1 | 7/2015 | Rosinko |
| 2015/0192120 A1 | 7/2015 | Rotem et al. |

FOREIGN PATENT DOCUMENTS

| | | |
|---|---|---|
| EP | 0225158 A2 | 6/1987 |
| EP | 0315312 A1 | 5/1989 |
| EP | 0429866 A1 | 6/1991 |
| EP | 0483794 A1 | 5/1992 |
| EP | 0858812 A2 | 8/1998 |
| EP | 1031358 A1 | 8/2000 |
| EP | 1350955 A2 | 10/2003 |
| EP | 1557186 | 7/2005 |
| EP | 1611834 A2 | 1/2006 |
| EP | 1485149 B1 | 7/2008 |
| FR | 2632529 A1 | 12/1989 |
| FR | 2753236 A1 | 3/1998 |
| JP | 60043188 A | 3/1985 |

(56) References Cited

FOREIGN PATENT DOCUMENTS

| | | |
|---|---|---|
| JP | 6-169992 A | 6/1994 |
| JP | 2002-57738 A | 2/2002 |
| JP | 2004141418 A | 5/2004 |
| WO | 1984000691 A1 | 3/1984 |
| WO | 9116933 A1 | 11/1991 |
| WO | 1991016933 A1 | 11/1991 |
| WO | 1993025816 A1 | 12/1993 |
| WO | 9408647 A1 | 4/1994 |
| WO | 1996003168 A1 | 2/1996 |
| WO | 1996030679 A1 | 10/1996 |
| WO | 1997034084 A1 | 9/1997 |
| WO | 1998004301 A1 | 2/1998 |
| WO | 1998013080 A2 | 4/1998 |
| WO | 1998047551 A1 | 10/1998 |
| WO | 99/58178 A1 | 11/1999 |
| WO | 2001039816 A2 | 6/2001 |
| WO | 2001065232 A1 | 9/2001 |
| WO | 2002036044 A2 | 5/2002 |
| WO | 2002038204 A2 | 5/2002 |
| WO | 2002049509 A2 | 6/2002 |
| WO | 2002068015 A2 | 9/2002 |
| WO | 03027503 A1 | 4/2003 |
| WO | 2003080158 A1 | 10/2003 |
| WO | 2004070548 A2 | 8/2004 |
| WO | 2004093648 A2 | 11/2004 |
| WO | 2005089263 A2 | 9/2005 |
| WO | 2006/056986 A1 | 6/2006 |
| WO | 2007133259 A1 | 11/2007 |
| WO | 2008036658 A2 | 3/2008 |
| WO | 2008059492 A2 | 5/2008 |
| WO | 2008059493 A2 | 5/2008 |
| WO | 2008059494 A2 | 5/2008 |
| WO | 2008059495 A2 | 5/2008 |
| WO | 2008059496 A2 | 5/2008 |
| WO | 2008059498 A2 | 5/2008 |
| WO | 2008059499 A2 | 5/2008 |
| WO | 2008130644 A1 | 10/2008 |
| WO | 2010053702 A1 | 5/2010 |
| WO | 2010053703 A1 | 5/2010 |
| WO | 2010091313 A2 | 8/2010 |
| WO | 2011128850 A2 | 10/2011 |
| WO | 2012095827 A1 | 7/2012 |
| WO | 2012095829 A2 | 7/2012 |
| WO | 2013001425 A2 | 1/2013 |
| WO | 2013/028704 A1 | 2/2013 |
| WO | 2013/090748 A1 | 6/2013 |

OTHER PUBLICATIONS

International Application PCT/IL2007/001398 Search Report dated Jun. 11, 2008 (2 pages).
International Application PCT/IL2007/001398 Patentability Report dated May 19, 2009 (6 pages).
International Application PCT/IL2007/001399 Search Report dated Jun. 4, 2008 (3 pages).
International Application PCT/IL2007/001399 Patentability Report dated May 19, 2009 (9 pages).
International Application PCT/IL2007/001400 Search Report dated Jul. 15, 2008 (3 pages).
International Application PCT/IL2007/001400 Patentability Report dated May 19, 2009 (10 pages).
International Application PCT/IL2007/001401 Search Report dated Sep. 24, 2008 (2 pages).
International Application PCT/IL2007/001401 Patentability Report dated May 19, 2009 (11 pages).
International Application PCT/IL2007/001402 Search Report dated Jun. 20, 2008 (3 pages).
International Application PCT/IL2007/001402 Patentability Report dated May 19, 2009 (4 pages).
International Application PCT/IL2007/001404 Search Report dated Jul. 14, 2008 (2 pages).
International Application PCT/IL2007/001404 Patentability Report dated May 19, 2009 (7 pages).
International Application PCT/IL2007/001405 Search Report dated Jul. 21, 2008 (4 pages).
International Application PCT/IL2007/001405 Patentability Report dated May 19, 2009 (7 pages).
International Application PCT/IL2005/001249 Search Report dated Apr. 5, 2006 (18 pages).
International Application PCT/IL1997/000289 Search report dated Jan. 27, 1998 (18 pages).
International Application PCT/IL1997/000290 Search Report dated Jan. 27, 1998 (18 pages).
International Application PCT/IL2003/000947 Search Report dated Mar. 3, 2004 (43 pages).
International Application PCT/IB2011/051586 Search Report dated Oct. 27, 2011 (3 pages).
International Application PCT/IB2011/051586 Patentability Report dated Oct. 16, 2012 (9 pages).
International Application PCT/IB2012/050192 Search Report dated Aug. 17, 2012 (2 pages).
International Application PCT/IB2012/050192 Patentability Report dated Jul. 16, 2013 (6 pages).
International Application PCT/IB2012/050189 Search Report dated May 30, 2012 (2 pages).
International Application PCT/IB2012/050189 Patentability Report dated Jul. 16, 2013 (5 pages).
International Application PCT/IB2012/053149 Search Report dated Jan. 15, 2013 (2 pages).
U.S. Appl. No. 09/125,438 Official Action dated May 3, 1999 (4 pages).
U.S. Appl. No. 09/125,438 Official Action dated Jul. 15, 1999 (7 pages).
U.S. Appl. No. 10/535,103 Official Action dated Feb. 2, 2009 (9 pages).
European Application No. 05810500.8 Official Action dated Jul. 6, 2009 (5 pages).
European Application No. 05810500.8 Response to Official Action dated Jul. 6, 2009, submitted Oct. 15, 2009 (8 pages).
European Application No. 05810500.8 Official Action dated Jan. 23, 2012 (4 pages).
European Application No. 05810500.8 Response to Official Action dated Jan. 23, 2012, submitted May 22, 2012 (6 pages).
U.S. Appl. No. 11/791,599 Official Action (Non-Final) dated Aug. 19, 2010 (16 pages).
U.S. Appl. No. 11/791,599 Response to Official Action (Non-Final) dated Aug. 19, 2010, submitted Jan. 11, 2011 (8 pages).
U.S. Appl. No. 11/791,599 Official Action (Final) dated Mar. 31, 2011 (13 pages).
U.S. Appl. No. 11/791,599 Response to Official Action (Final) dated Mar. 31, 2011, submitted May 23, 2011 (7 pages).
U.S. Appl. No. 11/791,599 Notice of Allowance dated Jun. 14, 2011 (5 pages).
U.S. Appl. No. 13/229,798 Official Action (Non-Final) dated Dec. 26, 2012 (10 pages).
U.S. Appl. No. 13/229,798 Response to Official Action (Non-Final) dated Dec. 26, 2012, submitted Mar. 21, 2013 (13 pages).
U.S. Appl. No. 13/229,798 Notice of Allowance dated Apr. 19, 2013 (6 pages).
U.S. Appl. No. 13/229,798 Notice of Withdrawal from Issue dated May 13, 2013 (1 page).
U.S. Appl. No. 13/229,798 Official Action (Non-Final) dated Jun. 21, 2013 (6 pages).
Chinese Patent Application No. 200580045471.3 "Finger-type peristaltic pump" Official Action dated Jul. 18, 2008 and English translation thereof (7 pages).
Chinese Patent Application No. 200780041966.8 Official Action dated Jul. 13, 2010 (7 pages).
Chinese Patent Application No. 200780041966.8 Response to Official Action dated Jul. 13, 2010, as submitted (6 pages).
Chinese Patent Application No. 200780041966.8, translation of Notification of Grant, dated Jan. 28, 2011 (2 pages).
U.S. Appl. No. 12/464,202 Official Action (Non-Final) dated Oct. 3, 2011 (7 pages).
U.S. Appl. No. 12/464,202 Response to Official Action (Non-Final) dated Oct. 3, 2011, submitted Feb. 12, 2012 (12 pages).

(56) References Cited

OTHER PUBLICATIONS

U.S. Appl. No. 12/464,202 Notice of Allowance dated Jul. 11, 2012 (5 pages).
U.S. Appl. No. 12/463,399 Official Action (Non-Final) dated Jul. 21, 2011 (15 pages).
U.S. Appl. No. 12/463,399 Response to Official Action (Non-Final) dated Jul. 21, 2011, submitted Oct. 21, 2011 (5 pages).
U.S. Appl. No. 12/463,399 Official Action (Final) dated Dec. 13, 2011 (7 pages).
U.S. Appl. No. 12/463,399 Response to Official Action (Final) dated Dec. 13, 2011, submitted Feb. 12, 2012 (10 pages).
U.S. Appl. No. 12/463,399 Advisory Action and Applicant Initiated Interview Summary dated Mar. 8, 2012 (8 pages).
U.S. Appl. No. 12/463,399 Response to Official Action (Final) dated Dec. 13, 2011, submitted Mar. 26, 2012 with Request for Continued Examination (13 pages).
U.S. Appl. No. 12/463,399 Notice of Allowance dated Apr. 29, 2013 (14 pages).
U.S. Appl. No. 12/514,310 Official Action (Non-Final) dated Jul. 21, 2011 (8 pages).
U.S. Appl. No. 12/514,310 Response to Official Action (Non-Final) dated Jul. 21, 2011, submitted Oct. 21, 2011 (8 pages).
U.S. Appl. No. 12/514,310 Official Action (Final) dated Jan. 20, 2012 (10 pages).
U.S. Appl. No. 12/514,310 Response to Official Action (Final) dated Jan. 20, 2012, submitted Apr. 25, 2012 with Request for Continued Examination (11 pages).
U.S. Appl. No. 12/514,310 Official Action (Non-Final) dated May 25, 2012 (7 pages).
U.S. Appl. No. 12/514,310 Response to Official Action (Non-Final) dated May 25, 2012, submitted Jun. 28, 2012 (6 pages).
U.S. Appl. No. 12/514,310 Notice of Allowance dated Aug. 22, 2012 (7 pages).
U.S. Appl. No. 12/514,311 Official Action (Non-Final) dated Sep. 16, 2010 (10 pages).
U.S. Appl. No. 12/514,311 Response to Official Action (Non-Final) dated Sep. 16, 2010, submitted Dec. 9, 2010 (23 pages).
U.S. Appl. No. 12/514,311 Official Action (Final) dated Feb. 18, 2011 (7 pages).
U.S. Appl. No. 12/514,311 Examiner Interview Summary Record dated Mar. 4, 2011 (4 pages).
U.S. Appl. No. 12/514,311 Response to Official Action (Final) dated Feb. 18, 2011, submitted Mar. 31, 2011 with Request for Continued Examination (9 pages).
European Patent Application No. 10192477.7 Search Report dated May 10, 2011 (5 pages).
European Patent Application No. 10192477.7 Response to Search Report dated May 10, 2011, submitted Dec. 28, 2011.
U.S. Appl. No. 12/644,026 Official Action (Non-Final) dated Apr. 6, 2012 (12 pages).
U.S. Appl. No. 12/644,026 Response to Official Action (Non-Final) dated Apr. 6, 2012, submitted Jul. 5, 2012 (11 pages).
U.S. Appl. No. 12/644,026 Notice of Allowance dated Oct. 11, 2012 (10 pages).
U.S. Appl. No. 13/742,454 Official Action (Non-Final) dated Oct. 7, 2013 (13 pages).
U.S. Appl. No. 12/644,027 Official Action (Non-Final) dated Apr. 28, 2011 (7 pages).
U.S. Appl. No. 12/644,027 Response to Official Action (Non-Final) dated Apr. 28, 2011, submitted Jul. 21, 2011 (10 pages).
U.S. Appl. No. 12/644,027 Notice of Allowance dated Nov. 17, 2011 (5 pages).
U.S. Appl. No. 13/229,798 Response to Official Action (Non-Final) dated Jun. 21, 2013, submitted Oct. 21, 2013 (3 pages).
U.S. Appl. No. 13/229,798 Notice of Allowance dated Nov. 14, 2013 (54 pages).
U.S. Appl. No. 13/651,420 Official Action (Non-Final) dated Nov. 4, 2013 (8 pages).
U.S. Appl. No. 13/651,420 Response to Official Action (Non-Final) dated Nov. 4, 2013, submitted Nov. 21, 2013 (2 pages).
U.S. Appl. No. 13/681,440 Official Action (Non-Final) dated Oct. 24, 2013 (11 pages).
U.S. Appl. No. 13/651,420 Official Action (Non-Final) dated Jan. 6, 2014 (8 pages).
U.S. Appl. No. 13/651,420 Response to Official Action (Non-Final) dated Jan. 6, 2014, submitted Mar. 5, 2014 (9 pages).
U.S. Appl. No. 13/651,420 Official Action (Final) dated Apr. 24, 2014 (8 pages).
U.S. Appl. No. 13/651,420 Response to Official Action (Final) dated Apr. 24, 2014, submitted Jul. 22, 2014 with Request for Continued Examination (15 pages).
U.S. Appl. No. 13/651,420 Official Action (Non-Final) dated Aug. 19, 2014 (10 pages).
U.S. Appl. No. 13/651,420 Response to Official Action (Non-Final) dated Aug. 19, 2014, submitted Dec. 18, 2014 (7 pages).
U.S. Appl. No. 14/016,105 Official Action (Non-Final) dated Oct. 15, 2014 (10 pages).
U.S. Appl. No. 13/681,440 Response to Official Action (Non-Final) dated Oct. 24, 2013, submitted Jan. 20, 2014 (10 pages).
U.S. Appl. No. 13/681,440 Official Action (Final) dated Feb. 14, 2014 (14 pages).
U.S. Appl. No. 13/681,440 Response to Official Action (Final) dated Feb. 14, 2014, submitted Jul. 14, 2014 with Request for Continued Examination (14 pages).
U.S. Appl. No. 13/681,440 Official Action (Non-Final) dated Sep. 2, 2014 (19 pages).
U.S. Appl. No. 12/514,311 Official Action (Non-Final) dated Oct. 7, 2014 (11 pages).
U.S. Appl. No. 13/742,454 Response to Official Action (Non-Final) dated Oct. 7, 2013, submitted Jan. 6, 2014 (7 pages).
U.S. Appl. No. 13/742,454 Official Action (Final) dated Mar. 28, 2014 (14 pages).
U.S. Appl. No. 13/742,454 Response to Official Action (Final) dated Mar. 28, 2014, submitted Jun. 29, 2014 with Request for Continued Examination (10 pages).
U.S. Appl. No. 13/742,454 Notice of Allowance dated Aug. 21, 2014 (10 pages).
U.S. Appl. No. 13/640,519 Official Action (Non-Final) dated Dec. 24, 2013 (7 pages).
U.S. Appl. No. 13/640,519 Response to Official Action (Non-Final) dated Dec. 24, 2013, submitted Jan. 16, 2014 (2 pages).
U.S. Appl. No. 13/640,519 Official Action (Non-Final) dated Mar. 20, 2014 (15 pages).
U.S. Appl. No. 13/640,519 Response to Official Action (Non-Final) dated Mar. 20, 2014, submitted Jun. 17, 2014 (14 pages).
U.S. Appl. No. 13/640,519 Official Action (Final) dated Oct. 1, 2014 (11 pages).
U.S. Appl. No. 13/924,572 Official Action (Non-Final) dated Dec. 2, 2014 (13 pages).
European Application No. 11768544.6 Supplementary Partial European Search Report dated Nov. 13, 2014 (7 pages).
European Application No. 12734200.4 Supplementary European Search Report dated Aug. 18, 2014 (6 pages).
European Application No. 05810500.8 Official Action dated Nov. 3, 2014 (5 pages).
European Application No. 05810500.8 Response to Official Action dated Nov. 3, 2014, submitted Mar. 9, 2015 (31 pages).
Indian Patent Application No. 2344KOLNP2007 Office Action dated Dec. 31, 2014 (2 pages).
Indian Patent Application No. 2344KOLNP2007 Response to Office Action dated Dec. 31, 2014, submitted Aug. 7, 2015 (19 pages).
U.S. Appl. No. 14/181,673 Official Action (Non-Final) dated Jun. 3, 2015 (12 pages).
U.S. Appl. No. 13/651,420 Official Action (Final) dated Mar. 16, 2015 (6 pages).
U.S. Appl. No. 13/651,420 Response to Official Action (Final) dated Mar. 16, 2015, submitted May 14, 2015 (5 pages).
U.S. Appl. No. 13/651,420 Official Action (Final) dated Jun. 9, 2015 (9 pages).
U.S. Appl. No. 14/016,105 Response to Official Action (Non-Final) dated Oct. 15, 2014, submitted Jan. 14, 2015 (7 pages).
U.S. Appl. No. 14/016,105 Notice of Allowance dated Feb. 17, 2015 (14 pages).

(56) References Cited

OTHER PUBLICATIONS

U.S. Appl. No. 13/681,440 Response to Official Action (Non-Final) dated Sep. 2, 2014, submitted Feb. 25, 2015 (12 pages).
U.S. Appl. No. 13/681,440 Official Action (Final) dated Apr. 24, 2015 (21 pages).
U.S. Appl. No. 12/514,311 Response to Official Action (Non-Final) dated Oct. 7, 2014, submitted Jan. 7, 2015 (5 pages).
U.S. Appl. No. 12/514,311 Official Action (Final) dated Apr. 20, 2015 (12 pages).
U.S. Appl. No. 12/514,311 Response to Official Action (Final) dated Apr. 20, 2015, submitted Jun. 21, 2015 (10 pages).
U.S. Appl. No. 12/514,311 Official Action (Advisory Action) dated Jul. 1, 2015 (8 pages).
U.S. Appl. No. 12/514,311 Response to Official Action (Advisory Action) dated Jul. 1, 2015, submitted Jul. 20, 2015 (8 pages).
U.S. Appl. No. 12/514,311 Official Action (Advisory Action) dated Aug. 5, 2015 (6 pages).
European Application No. 10192477.7 Official Action dated Jul. 6, 2015 (5 pages).
European Application No. 11768544.6 Response to Official Action dated Dec. 2, 2014, submitted May 29, 2015 (12 pages).
U.S. Appl. No. 13/640,519 Response to Official Action (Final) dated Oct. 1, 2014, submitted Dec. 28, 2014 (15 pages).
U.S. Appl. No. 13/640,519 Official Action (Non-Final) dated May 6, 2015 (13 pages).
European Application No. 12734200.4 Response to Official Communication dated Sep. 4, 2014, submitted Mar. 4, 2015 (16 pages).
U.S. Appl. No. 13/978,538 Official Action (Non-Final) dated Jan. 23, 2015 (24 pages).
U.S. Appl. No. 13/978,538 Response to Official Action (Non-Final) dated Jan. 23, 2015, submitted May 21, 2015 (13 pages).
U.S. Appl. No. 13/978,538 Official Action (Non-Final) dated Jul. 24, 2015 (16 pages).
European Application No. 12805094.5 Supplementary Partial European Search Report dated Feb. 23, 2015 (8 pages).
European Application No. 12805094.5 Response to Supplementary Partial European Search Report submitted Apr. 2, 2015 (1 page).
European Application No. 12805094.5 Supplementary European Search Report dated Jun. 30, 2015 (14 pages).
U.S. Appl. No. 13/924,572 Response to Official Action (Non-Final) dated Dec. 2, 2014, submitted Mar. 26, 2015 (11 pages).
U.S. Appl. No. 13/924,572 Official Action (Non-Final) dated May 14, 2015 (12 pages).
PCT Appl. No. PCT/IB14/62106 International Search Report and Written Opinion dated Feb. 24, 2015 (8 pages).
PCT Appl. No. PCT/IB15/50873 International Search Report and Written Opinion dated Jun. 25, 2015 (8 pages).

* cited by examiner

FINGER TYPE PERISTALTIC PUMP COMPRISING A RIBBED ANVIL

FIELD OF THE INVENTION

The present invention generally relates to a finer-type peristaltic infusion pump comprising a ribbed anvil rigidly accepting a flexible infusion tube when it is pressed by a pressing-finger

BACKGROUND OF THE INVENTION

This invention relates to a design using ribs on the pumping substrate of a peristaltic pump. At present peristaltic pumps find use in medical settings to add nutrients to blood, to force blood through filters to clean it as in dialysis, or to move blood through the body and lungs during open heart surgery. They are advantageous in these situations since the pump elements do not contact the pumped fluid, eliminating any possibility of contamination. Additionally the pumping action is gentle enough that blood cells are not damaged. Further uses include pumping aggressive chemicals, high solids slurries and other materials where isolation of the product from the environment, and the environment from the product, are critical. As the operation of such a pump can be critical for life support, they are generally provided with battery back up. The efficiency of the device thus becomes an important parameter since the length of time it can remain in operation while on battery power is limited by its efficiency.

SUMMARY OF THE INVENTION

It is thus the object of the present invention to provide a finer-type peristaltic pump (DDS) comprising a plurality of pressing-fingers, infusion-tube, and a passive interface mechanism; wherein this passive interface mechanism comprising (a) a means for accommodating said flexible infusion tube and mounting the same in a location suitable for said pressing-fingers to apply an approximated tangential force on said tube to squeeze it; (b) a ribbed anvil rigidly accepting said flexible tube when it is pressed by said finger; and further wherein said anvil comprising one or more of the following (i) a plurality of ribs facing said fingers' tip, (ii) a plurality of ribs located in between said fingers, or (iii) any combination thereof.

Another object is to provide a DDS as defined above, wherein one or more of said ribs is of a different height as compared with others ribs (reference ribs), so as the squeezed volume of the infused fluid per pumping cycle provided by said one or more ribs is either bigger or smaller height as compared with squeezed volume provided by said reference ribs.

Another object is to provide a DDS as defined above, wherein one or more of said ribs is of a different width as compared with others ribs (reference ribs), so as less pressing force is required by a given finger for shutting off said infusion tube against narrower ribs as compared with reference ribs, and vice versa, more pressing force is required by a given finger for shutting off said infusion tube against wider ribs as compared with reference ribs.

Another object is to provide a DDS as defined above, especially adapted to provide optimization means for calibrating each finger's force requirements per single pumping cycle by widening or narrowing adjacent rib's width.

Another object is to provide a DDS as defined above, wherein one or more of said ribs is of a different specifications: namely width and/or profile characteristics as compared with others ribs (reference ribs), in the manner that less pressing force is required by a given finger for shutting off said infusion tube against said ribs as compared with said reference ribs, so as minimized tube's degradation is provided due to continuous shutting off of the flexible tube by said fingers pressing tips.

Another object is to provide a method of obtaining a predetermined flow capacity, comprising of obtaining a DDS as defined in any of the above; and adjusting the specifications one or more of said ribs, namely altering its width and/or profile characteristics, hence accepting a respectively wide range of infusion-tubes types, flexibility, conditions and diameters, with no requirement of controlling pump's pumping parameters

BRIEF DESCRIPTION OF THE FIGURES

In order to understand the invention and to see how it may be implemented in practice, a plurality of preferred embodiments will now be described, by way of non-limiting example only, with reference to the accompanying drawing, in which FIG. 1 schematically illustrating an out-of-scale and simplified lateral cross-section of tube pressing mechanism in a finger-type infusion-pump according to one embodiment of the present invention.

DETAILED DESCRIPTION OF THE INVENTION

The following description is provided, alongside all chapters of the present invention, so as to enable any person skilled in the art to make use of said invention and sets forth the best modes contemplated by the inventor of carrying out this invention. Various modifications, however, will remain apparent to those skilled in the art, since the generic principles of the present invention have been defined specifically to provide a finer-type peristaltic pump comprising a ribbed anvil rigidly accepting a flexible infusion tube when it is pressed by a pressing-finger.

The term 'plurality' refers hereinafter to any integer number equal or higher 1, e.g., 2 to 10, especially 2 to 4.

The present invention pertains to finger-type peristaltic pump (DDS) that utilizes a passive mechanical interface adapted to incorporate a set of infusion tubing with a pumping mechanism and various sensors, wherein the back portion of the mechanical interface is provided as an anvil accepting those M pressing fingers.

The term passive interface relates to a mechanical interface of the set tubing to the DDS that has no moving parts or static members being an integral part of the aforesaid pumping mechanism of sensors thereof, e.g., pistols, hinges, cams, wheels, sealing membranes, gaskets etc. A plurality of N ribs is located inside said back-portion of the interface. A portion of the ribs ($n_1$) is located below the fingers tips, and a portion ($n_2$) is located in between those fingers. N and M are any integer numbers, wherein $n_1$ is either equal or different then $n_2$. It is acknowledged in this respect that according to one possible embodiment of the present invention, no ribs are located under the fingers. The ribs provide useful means for calibrating the flowing volume in said tube in each pumping cycle. The ribs further provide useful means for an individual calibration of the force requires by each of the pressing fingers to complete shutoff of the infusion tube. The ribs further allow optimization of the energy consumes to shutoff the tube and the energy requires allowing fluids flow in said tube. The ribs also provide useful means for minimizing degradation of the infusion tube, especially by optimizing the surfaces of the finger tips continuously pressing the tube. Moreover, the present invention also provides useful means for energy optimization. Lastly, the ribs facilitate the immobilization the infusion tube by mechanical interface of the pressing fingers, e.g., to approach a relatively wide range of tubes (diameter, elasticity, regulatory of the surface etc) so as a constant volume of fluid is pumped per a given pumping cycle.

Figure 1:
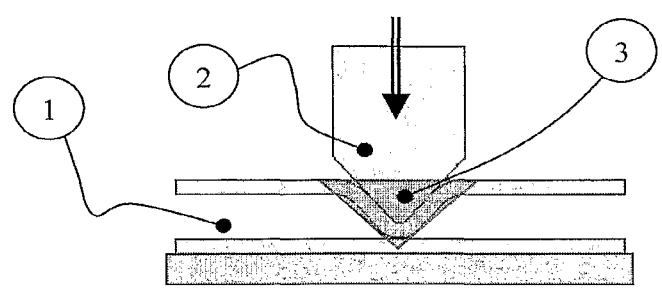
Figure 2:
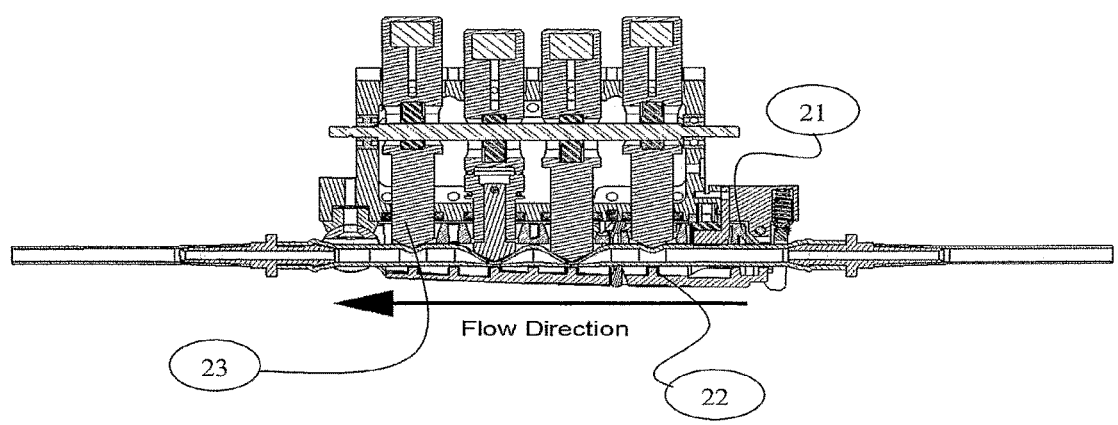
FIG. 2 schematically illustrating a detailed lateral cross-section of the pressing fingers and infusion tube in an infusion-pump according to one embodiment of the present invention; and, FIG. 3 schematically illustrating two out-of-scale and simplified lateral cross-sections of a pressing mechanism as defined above; higher view comprises of a non-ribbed anvil (prior art), and lower view comprises ribbed-anvil according to one embodiment of the present invention.

Controlling the volume of fluid is pumped per a given pumping cycle: Reference is now made to FIGS. 1 and 2, wherein FIG. 1 schematically illustrates an out of scale lateral cross section of an infusion tube (1), wherein a perpendicular peristaltic finger (2) is reversibly mounted and pressing the same so as a measurable volume of fluid (3) is squeezed due to the tube's shutoff. Hence, squeezed volume (3) is regulated by the pressing finger (2). Some of the fluid (3) is pressed upstream and some is pressed downstream. The volume of upstream pressed fluid (against an adjacent tube's shutoff provided by a neighboring pressing finger) is dependent on the flexibility of the tube and on the existence of rigid envelops accommodating the tube and restricting its inflation. It is acknowledged in this respect that in an extreme case, a very flexible tube is utilized; the diameter of this flexible tube is not restricted by a rigid envelope, so as by providing a high pressure zone downstream to the press, most of the fluid is pressed backwards and not forwards. It is hence in the scope of the present invention wherein regulation of geometry of the mechanical interface of a finger-type peristaltic pumps, tube's inflation can be regulate and backwards flow of fluid at each pumping cycle can be avoided. As a result, one can optimize the volume of fluid to be pump per a given pumping cycle and minimize losses obtained by upstream flow of the fluid.

FIG. 2 schematically illustrates an out-of-scale lateral cross section of a finger-type peristaltic pump that comprises a plurality of 4 fingers being rotatably mounted perpendicular to an infusion tube. A mechanical interface (21) avoids inflation of the tube along the pumping and provides exact regulation of the volume of the squeezed fluid at each pumping cycle. By determining the measurements of the ribs (22) under the pressing fingers, an exact calibration of the force require to shutoff the tube by each finger (23) is provided.

Optimization of Energy Requires to Shutoff the Infusion Tube vs Energy Requires to Facilitate a Fluid Flow Thorough this Tube The pumping fingers are adapted to apply an approximately perpendicular force on the flexible infusion tube to squeeze it, so as one of its walls will bend and touch the opposite wall and fluids flow will shutoff In theory a continues contact line between the tube walls will produce a complete shutoff, however grater force is needed to produces a pressure—on the tube walls—high enough to overcome tube's surface irregularities. It is acknowledged that smaller pressing area in the aforesaid tube's shutoff location requires less force. Upper zoomed-in scheme presents a case of the prior art whereat pressing-forces are spread upon the flexible tube, more area is to be squeezed and hence stronger forces are to be applied; wherein lower zoomed-in scheme presents a case according to one embodiment of the present invention wherein pressing forces are focused towards the rib and less force is required for complete shut off of the infusion tube.

Figure 3:
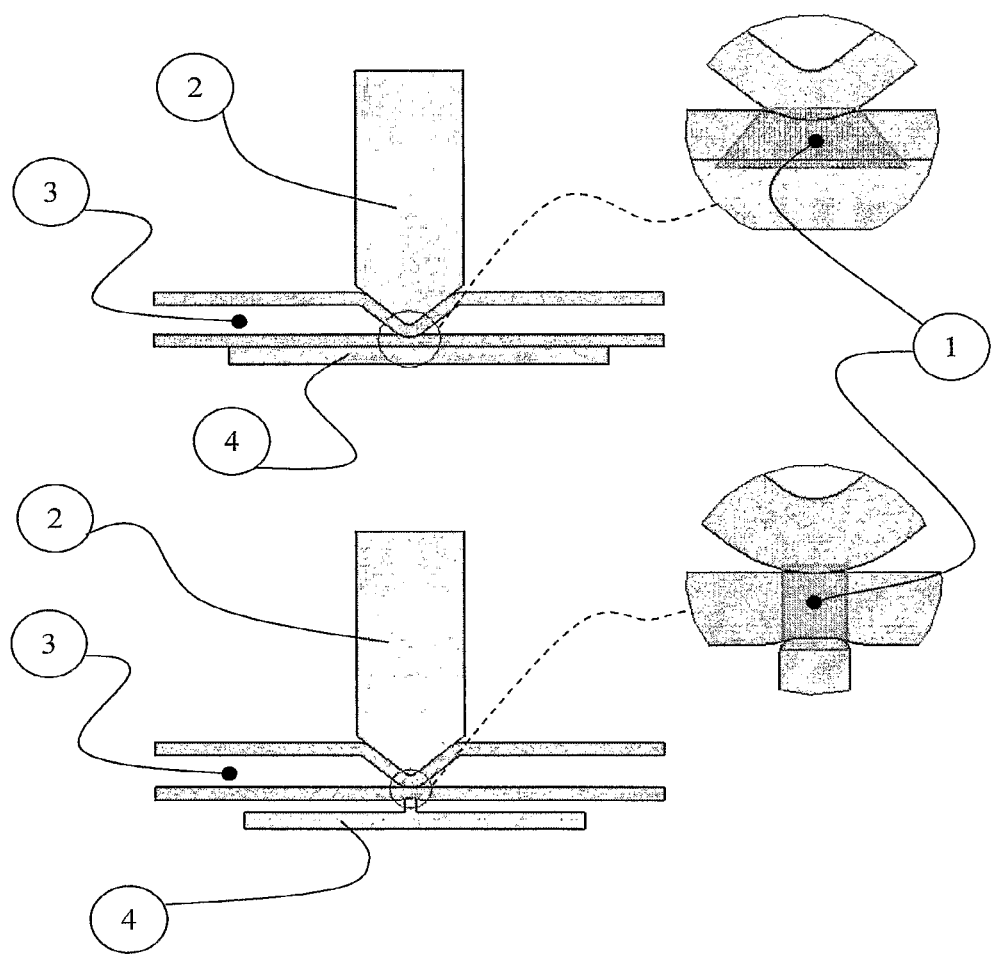

Reference is now made to FIG. 3, schematically illustrating out-of-scale lateral cross sections of pressing mechanism of finger-type peristaltic pumps that comprise a pressing-finger (2) which presses tube (3) towards an anvil (4) at a given pressing area (1). Higher illustrations present a plain anvil (4) (See also wide pressing area at the zooming view on the right); wherein lower illustrations present a ribbed anvil with respectively narrow pressing area at the zooming view on the right.

It is in the scope of the invention wherein the capacity of the flow can be calibrated, e.g., by adjusting the width or other proportions of one or more ribs. Similarly, the force which is required to provide an optimal flow capacity can be calibrated and adjusted. The proportions of length and width of ribs under the pressing fingers, rib's profile and cross sections, as well as other dimensions of the rids in the passive interface mechanism, allow the optimization of capacity to flow ratio. The height of the ribs under the pressing fingers provides for calibration of the sealing properties of eh mechanism. A method of calibrating the fluid's flow capacity is also disclosed, and comprised of steps of adjusting the proportions of the ribs under the pressing fingers as defined above.

The invention claimed is:
1. An interface configured to be placed in conjunction with a finger-type peristaltic pump including a plurality of fingers, said pump having a pumping cycle of alternating linear motion of each finger, said interface comprising:
   a conduit having a compressible segment and positioned within said interface such that when said interface is mounted on the pump the alternating linear motion of the fingers causes fluid to flow through the conduit by applying a series of compressive forces on said conduit, thereby defining a set of contact points on the conduit where fingers of the pump contact the conduit during the alternating linear motion of the fingers;
   a conduit accommodation configured to receive said conduit and removably mount said interface to the finger type peristaltic pump; and
   a ribbed anvil positioned within said interface so as to contact a first surface of said conduit opposite a second surface of the conduit contacted by the fingers and having a longitudinal dimension perpendicular to the linear motion of the fingers, said ribbed anvil comprising:
   (i) a first set of protruding ribs positioned directly across from each of the contact points, each of said first set of ribs having a flat surface perpendicular to the linear motion of the fingers configured to provide a counterforce to a compressive force produced by each of the plurality of fingers, when said interface is mounted to the pump; and
   (ii) a second set of protruding ribs positioned such that the ribs of said second set of ribs alternate with the ribs of said first set of ribs, and such that the ribs of said second set of ribs are positioned to interface with the first surface of said conduit opposite the second surface of the conduit contacted by the fin- gers in between said contact points wherein said second set of ribs is configured to support the conduit when compressed.

2. The interface of claim 1, wherein the conduit further comprises a tube.

3. The interface of claim 1, wherein the conduit includes a silicon element.

4. The interface of claim 1, wherein the fingers are configured to cause fluid to flow through the conduit in substantially a first direction and the ribbed anvil is configured to limit fluid from flowing in substantially the opposite direction.

5. The interface of claim 1, wherein, at one of the first set of ribs are of changing height thus enabling calibrating the squeezed volume of the infused fluid per pumping cycle.

6. The interface according to claim 5, wherein at least one rib of said first set of ribs has a different width than other ribs of said first set of ribs.

7. The interface according to claim 1, further comprising at least one of the active elements from the group consisting of: a pistol, a hinge, a cam, a wheel, a sealing membrane and a gasket.

8. The interface of claim 1, wherein the first and second set of ribs do not directly contact said conduit.

9. A system for pumping fluid through a conduit, said system comprising:
   a finger-type peristaltic pump including a plurality of fingers having an elongated body and pointed ends, said pump having a pumping cycle of alternating linear motion of each finger; an interface comprising:
     a housing configured to removably mount to the finger type peristaltic pump, said housing further configured to receive a conduit within said housing, the conduit having a compressible segment and positioned within said housing such that when said housing is mounted on the pump, the alternating linear motion of the fingers causes fluid to flow through the conduit by the pointed ends applying a series of compressive forces on said conduit, thereby defining a set of contact points on the conduit where the pointed ends of the fingers contact the conduit during the alternating linear motion of the fingers; and
     a ribbed anvil positioned within said housing so as to contact a first surface of said conduit opposite a second surface of the conduit contacted by the fingers and having a longitudinal dimension perpendicular to the linear motion of the fingers the ribbed anvil comprising:
       a first set of protruding ribs positioned across from the contact points and each of said first set of ribs having a flat surface perpendicular to the linear motion of the fingers narrower than a width of said elongated body configured to provide a counter-force to compressive forces produced by the plurality of fingers, when said housing is mounted to the pump; and
       a second set of protruding ribs positioned such that the ribs of said second set of ribs alternate with the ribs of said first set of ribs, and such that the ribs of said second set of ribs are positioned to interface with the first surface of said conduit opposite the second surface of the conduit contacted by the fingers in between said contact points wherein said second set of ribs is configured to support the conduit when compressed.

10. The interface of claim 9, wherein the conduit further comprises a tube.

11. The interface of claim 9, wherein the conduit includes a silicon element.

12. The interface of claim 9, wherein the fingers are configured to cause fluid to flow through the conduit in substantially a first direction and the ribbed anvil is configured to limit fluid from flowing in substantially the opposite direction.

13. The interface of claim 9, wherein, at one of the first set of ribs are of changing height thus enabling calibrating the squeezed volume of the infused fluid per pumping cycle.

14. The interface according to claim 13, wherein at least one rib of said first set of ribs has a different width than other ribs of said first set of ribs.

15. The interface according to claim 9, further comprising at least one of the active elements from the group consisting of: a pistol, a hinge, a cam, a wheel, a sealing membrane and a gasket.

* * * * *